United States Patent
Fang et al.

(10) Patent No.: US 11,147,748 B2
(45) Date of Patent: Oct. 19, 2021

(54) COMPOSITION OF TEMPORARY CROWN MATERIALS

(71) Applicant: National Taipei University of Technology, Taipei (TW)

(72) Inventors: Hsu-Wei Fang, Taipei (TW); Yuan-Min Lin, Taipei (TW); Meng-Chun Lin, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 0 days.

(21) Appl. No.: 16/654,136

(22) Filed: Oct. 16, 2019

(65) Prior Publication Data

US 2021/0059906 A1 Mar. 4, 2021

(30) Foreign Application Priority Data

Aug. 30, 2019 (TW) ................. 108131444

(51) Int. Cl.
*A61K 6/887* (2020.01)
*C08L 33/12* (2006.01)
*A61C 5/77* (2017.01)
*A61K 6/60* (2020.01)
*C08K 5/11* (2006.01)
*C08K 5/00* (2006.01)
*C08K 5/14* (2006.01)

(52) U.S. Cl.
CPC ............. *A61K 6/887* (2020.01); *A61C 5/77* (2017.02); *A61K 6/60* (2020.01); *C08L 33/12* (2013.01); *C08K 5/0016* (2013.01); *C08K 5/11* (2013.01); *C08K 5/14* (2013.01)

(58) Field of Classification Search
CPC .................................... A61K 6/887
See application file for complete search history.

(56) References Cited

U.S. PATENT DOCUMENTS

| 4,588,583 | A | * | 5/1986 | Pietsch | ............... | A61L 24/0021 |
| | | | | | | 514/772.4 |
| 4,910,259 | A | * | 3/1990 | Kindt-Larsen | ........ | A61L 24/001 |
| | | | | | | 525/259 |
| 2012/0302657 | A1 | * | 11/2012 | Moszner | ............... | A61K 6/887 |
| | | | | | | 522/24 |

OTHER PUBLICATIONS

Author Unknown, Internet Article, URL:https://woundmaster.blogspot.com/2018/02/blog-post_25.html, Feb. 25, 2018, 2 pages (with English translation).
Gutierrez-Villarreal et al., "The Effect of Citrate Esters as Plasticizers on the Thermal and Mechanical Properties of Poly(Methyl Methacrylate)," Journal of Applied Polymer Science, vol. 105, 2007, pp. 2370-2375.
Wang, "Correlation between Morphology and Mechanical Properties of Denture Resins Cured by Different Methods," Master Thesis, National Sun Yat-Sen University, retrieved Apr. 5, 2020, pp. 1-105 (120 pages total) with Abstract.

* cited by examiner

*Primary Examiner* — Michael F Pepitone
(74) *Attorney, Agent, or Firm* — Birch, Stewart, Kolasch & Birch, LLP

(57) ABSTRACT

The present invention is directed to a composition of temporary crown materials, comprising a powder reagent and a liquid reagent; wherein the powder reagent comprises PMMA and an initiator, and the liquid reagent comprises MMA, a catalyst, and a plasticizer; wherein the plasticizer is a citrate ester compound. The composition of temporary crown materials of the present invention has high hardness, high toughness, high flexural strength and excellent biocompatibility.

9 Claims, 6 Drawing Sheets

(A)

(B)

COMPOSITION OF TEMPORARY CROWN MATERIALS

This application claims priority under 35 U.S.C. § 119 to Application No. 108131444 filed in Taiwan on Aug. 30, 2019, the entire contents of all of which are expressly incorporated by reference into the present application.

BACKGROUND OF THE INVENTION

Field of the Invention

The present invention relates to a composition of temporary crown materials and, in particular, to a composition of temporary crown materials using a citrate ester as a plasticizer.

Description of the Prior Art

The temporary crowns are crowns for wearing, can be used for about 1 week to 3 months, and can properly maintain the function of dental occlusion. The main users are those who receive root canal treatment or dental implants, suffer from periodontal disease, or wear crowns. According to the statistics, among those who are over 65 years old, up to 75.3% of the elders has missing teeth. With the trend of aging society, the demand for temporary crowns is bound to increase.

The plasticizer in the temporary crown is a key material for the performance of the temporary crown. The most widely used crown plasticizer is the phthalate ester compound, such as dibutyl phthalate (DBP). However, due to the biological toxicity, DBP may cause destruction of thyroxine and growth hormones, affects the development of reproductive organs, and is difficult to decompose in the environment. Therefore, many countries (including Taiwan) have prohibited or restricted its addition to low concentrations, for example, a usage of no more than 0.1%.

Therefore, it is necessary to develop a temporary crown material that does not contain a phthalate ester compound and has good plasticizing effect and biocompatibility simultaneously to reduce the harm to the human body by temporary crowns.

SUMMARY OF THE INVENTION

In order to solve the foregoing problems and achieve the object of the invention, the present invention provides a composition of a temporary crown material, which comprises a powder reagent and a liquid reagent; wherein the powder reagent comprises poly methyl methacrylate (PMMA) and an initiator; the liquid reagent comprises methyl methacrylate, a catalyst, and a plasticizer; wherein the plasticizer is a citrate ester compound.

In one embodiment of the invention, the plasticizer is triethyl citrate or acetyl tributyl citrate.

In one embodiment of the invention, the initiator is benzoyl peroxide (BPO).

In one embodiment of the invention, the catalyst is N,N-dimethyl-p-toluidine (DMPT).

In one embodiment of the invention, the ratio of the powder reagent to the liquid reagent is between 3:1 and 1:1 (W/V).

In one embodiment of the present invention, the powder reagent comprises 60-90% poly methyl methacrylate (PMMA), 0-5% benzoyl peroxide (BPO), 0-1% pigment, 0-1% opacifier, 0-20% plasticizer, and the rest being inorganic particles.

In an embodiment of the present invention, the liquid reagent comprises 1-5% catalyst, 0-20% crosslinking agent, 0-20% plasticizer, 0-0.1% inhibitor, 5-10% organic solvent, 5-10% UV absorber, and the rest being methyl methacrylate monomer (MMA).

In one embodiment of the invention, the percentage of the plasticizer is between 2% and 10%.

In another aspect, the present invention provides a method for preparing a temporary crown, comprising:

providing poly methyl methacrylate and an initiator, which are mixed to form a powder reagent;

providing methyl methacrylate, a catalyst, and a plasticizer, which are mixed to form a liquid reagent;

mixing the powder reagent with the liquid reagent to obtain a mixture; and placing the mixture at room temperature, which allows the mixture to cure, thereby obtaining a temporary crown.

In one embodiment of the present invention, the powder reagent and the liquid reagent are mixed and placed at 20° C. to 25° C. to wait for the formation of the temporary crown.

DETAILED DESCRIPTION OF THE EMBODIMENTS

Figure 1:
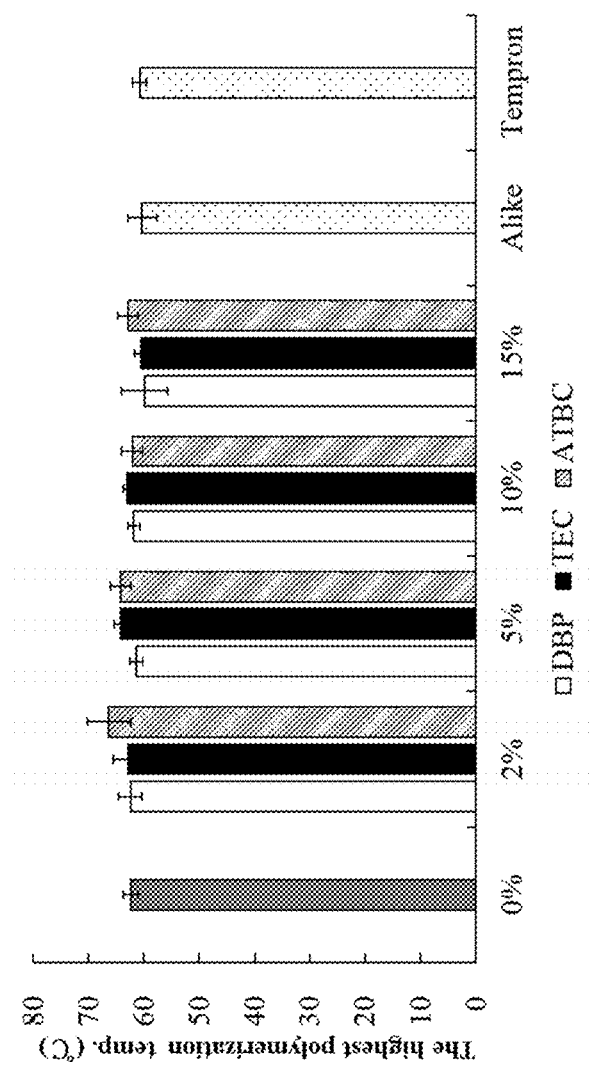
FIG. 1 shows the highest polymerization temperature test results of the temporary crown material compositions of the present invention.

The technical features of the present invention, including the specific features, are disclosed in the claims. For best understanding the technical features of the present invention, the present invention will be illustrated in detail as follows in conjunction with the specification, the embodiments according to the principle of the present invention as well as the drawings.

All the technical and scientific terms used in the specification and claims of the present invention have the definitions known by those of ordinary skill in the art, unless otherwise defined. All the singular terms "a", "an", "the" or their similar terms refer to more than one referent, unless otherwise indicated. The terms "or", "as well as" and "and" as used in the specification refer to "or/and", unless otherwise indicated. In addition, the terms "comprising" and "including" are open-ended transitions without limitations. The foregoing definitions are merely illustrative of the referents of the definitions of the terms and should not be construed as limiting the subject of the invention. Unless otherwise indicated, the materials used in the present invention are commercially and readily available.

Throughout the specification, unless otherwise indicated, the symbol of percentage (%) refers to the weight percentage (W/W).

The term "initiator" as used in the specification refers to a substance which cleaves and forms free radical ions upon being exposed to heat to cause polymerization of the monomers in the liquid reagent, and includes but is not limited to benzoyl peroxide (BPO) or diisobutylazonitrile.

The term "hardening" or "curing" as used in the specification refers to a reaction in which the physical properties of a composition, such as viscosity or hardness, change over time due to the chemical reactions between the components.

The term "plasticizer" as used in the specification refers to a substance that does not directly participate in the polymerization but is uniformly distributed inside the resin after polymerization to interfere with the interaction and bonding of the polymer molecules. The plasticizer is softer than pure polymer without plasticizer, thereby resisting internal stresses due to chewing. The possible plasticizer includes, but is not limited to, triethyl citrate (TEC) or acetyl tributyl citrate (ATBC).

The term "crosslinking agent" as used in the specification refers to a substance that is capable of forming bonding between linear molecules, thereby making plural linear molecules bond and crosslink with each other to form a network structure and to promote or regulate covalent or ions bonds between polymer molecular chains. The crosslinking agent includes, but is not limited to, ethylene glycol dimethacrylate (EGDMA).

The term "catalyst" as used in the specification refers to a substance which accelerates the decomposition of the initiator at room temperature and thereby increases the polymerization rate of the monomers, including but not limited to N,N-dimethyl-p-toluidine (DMPT), N,N-dihydroxyethyl-para-toluidine, or sulfonic acid.

The term "inhibitor" as used in the specification refers to a substance that sustains the shelf life of a material and reduces the premature occurrence of polymerization, such as hydroquinone.

The term "organic solvent" as used in the specification refers to a substance which mix the components of the liquid reagent homogeneously, such as methanol, ethanol, or propanol.

The term "ultraviolet (UV) absorber" as used in the specification is a substance that is able to filter out harmful ultraviolet light to retard the aging rate of a product, including but not limited to ethyl 2-cyano-3,3-diphenylacrylate.

The term "opacifier" as used in the specification is used to make the color of a temporary crown similar to that of an existing tooth; for example, titanium dioxide.

The term "inorganic particles" as used in the specification includes, but is not limited to, silicon carbide or aluminum oxide.

The term "pigment" as used in the specification refers to a substance added to make the color similar to the patient's existing teeth, such as iron oxide.

The present invention provides a composition of a temporary crown material, which has high hardness, high toughness, high flexural strength, and excellent biocompatibility.

The present invention overcomes the disadvantages of the prior art by replacing the phthalate ester with a citrate ester compound, which serves as a plasticizer in the composition of the temporary crown material. Therefore, the obtained temporary crowns not only have excellent flexural strength and biocompatibility, but also comply with international standards.

The present invention provides a composition of a temporary crown material, which comprises: a powder reagent and a liquid reagent; wherein the powder reagent comprises poly methyl methacrylate (PMMA) and an initiator; the liquid reagent comprises methyl methacrylate, a catalyst, and a plasticizer; wherein the plasticizer is a citrate ester compound.

In a specific embodiment of the invention, the citrate ester compound is triethyl citrate (TEC) or acetyl tributyl citrate (ATBC).

The composition of the temporary crown material of the present invention is characterized by excluding the phthalate ester compound.

According to an embodiment of the present invention, the pigment is iron oxide; the opacifier is titanium dioxide; the plasticizer is a citrate ester or a phthalate ester; and the inorganic particles are silicon carbide or alumina particles.

According to a preferred embodiment of the present invention, the powder reagent comprises 60-90% PMMA, 0-2% BPO, 0-1% pigment, 0-1% opacifier, 0-20% plasticizer, and the rest being inorganic particles.

According to a more preferred embodiment of the present invention, the powder reagent comprises 99% PMMA and 1% BPO.

According to the present invention, the liquid reagent comprises methyl methacrylate (MMA) and N,N-dimethyl-p-toluidine (DMPT) as a catalyst. In a specific embodiment, the liquid reagent may further include a crosslinking agent such as ethylene glycol dimethacrylate (EGDMA); a plasticizer such as DBP, triethyl citrate (TEC), or acetyl tributyl citrate (ATBC); an inhibitor such as hydroquinone; an organic solvent such as methanol; and an UV absorber such as ethyl 2-cyano-3,3-diphenylacrylate.

According to the present invention, the liquid reagent further comprises 1-5% catalyst, 0-20% crosslinking agent, 0-20% plasticizer, 0-0.1% inhibitor, 5-10% organic solvent, 5-10% UV absorber, and the rest being MMA.

According to a more preferred embodiment of the present invention, the liquid reagent comprises 1% DMPT, 5% methanol, 1% ethyl 2-cyano-3,3-diphenylacrylate, the crosslinking agent, the plasticizer, and the rest being MMA.

According to the present invention, the liquid reagent further comprises 0-15% TEC or ATBC as the plasticizer.

In one embodiment of the present invention, the plasticizer is 0-15%; preferably 2%-10%, more preferably 2%-5% TEC or ATBC.

In a preferred embodiment of the present invention, the crosslinking agent is 0-20% EGDMA.

According to the present invention, the liquid reagent comprises methyl methacrylate (MMA), a catalyst, and a plasticizer.

In a preferred embodiment of the present invention, the catalyst is N,N-dimethyl-p-toluidine (DMPT).

In a preferred embodiment of the present invention, the liquid reagent comprises 1-5% catalyst, 0-20% crosslinking agent, 0-20% plasticizer, 0-0.1% inhibitor, 5-10% organic solvent, 5-10% UV absorber, and the rest being methyl methacrylate monomer (MMA).

In a more preferred embodiment of the present invention, the liquid reagent comprises 1% DMPT, 5% methanol, 1% ethyl 2-cyano-3,3-diphenylacrylate, 0-10% crosslinking agent (such as EGDMA), 0-10% plasticizer (such as TEC or ATBC), and the rest being MMA.

In a preferred embodiment, the ratio of the powder reagent to the liquid reagent is between 3:1 and 1:1 (weight: volume (W/V)). In a more preferred embodiment, the ratio of the powder reagent to the liquid reagent is 2:1 (W/V).

In another aspect, the present invention provides a method for preparing a temporary crown, which comprises: providing poly methyl methacrylate and an initiator, which are mixed to form a powder reagent; providing methyl methacrylate, a catalyst, and a plasticizer, which are mixed to form a liquid reagent; mixing the powder reagent with the liquid reagent to obtain a mixture; and placing the mixture at room temperature, which allows the mixture to cure, thereby obtaining a temporary crown.

In a preferred embodiment, the powder reagent and the liquid reagent are mixed and placed at 20° C. to 25° C. to wait for the formation of the temporary crown.

In a preferred embodiment, the curing time of the mixture is from 100 to 500 seconds, preferably from 180 to 250 seconds after mixing.

Example 1 Preparation Method of a Temporary Crown

First, a powder reagent was prepared, which comprised 99% poly methyl methacrylate (PMMA) as a polymer and 1% benzoyl peroxide (BPO) as an initiator.

Afterwards, a liquid reagent was prepared, which comprised 1% DMPT, 5% methanol, 1% ethyl 2-cyano-3,3-diphenylacrylate, a crosslinking agent, a plasticizer, and the rest being MMA; wherein the crosslinking agent was 0-20% EGDMA, and the plasticizer was 0-15% TEC or ATBC.

The ratio of the powder reagent to the liquid reagent was between 3:1 and 1:1 (weight: volume (W/V)), for example 2:1 (W/V). The powder reagent and the liquid reagent were mixed, stirred, and then placed at room temperature, around 20° C. to 25° C., and passed the following periods of time: mixing period (the twentieth to forty-fifth seconds after mixing), polymerization period (the fiftieth to one hundredth seconds), lump period (the ninetieth to one hundred and fortieth seconds) and curing period (the one hundred and eightieth to two hundred and fiftieth seconds) to form a temporary crown.

FIG. 1 shows the highest polymerization temperature test results of the temporary crown material compositions. It can be seen from FIG. 1 that if the temporary crowns are prepared at room temperature (22±1° C.), the type of plasticizer (DBP, TEC, ATBC) has no significant effect on the polymerization temperature of the crown material. The highest polymerization temperature is around 60° C. to 70° C.

Figure 2:
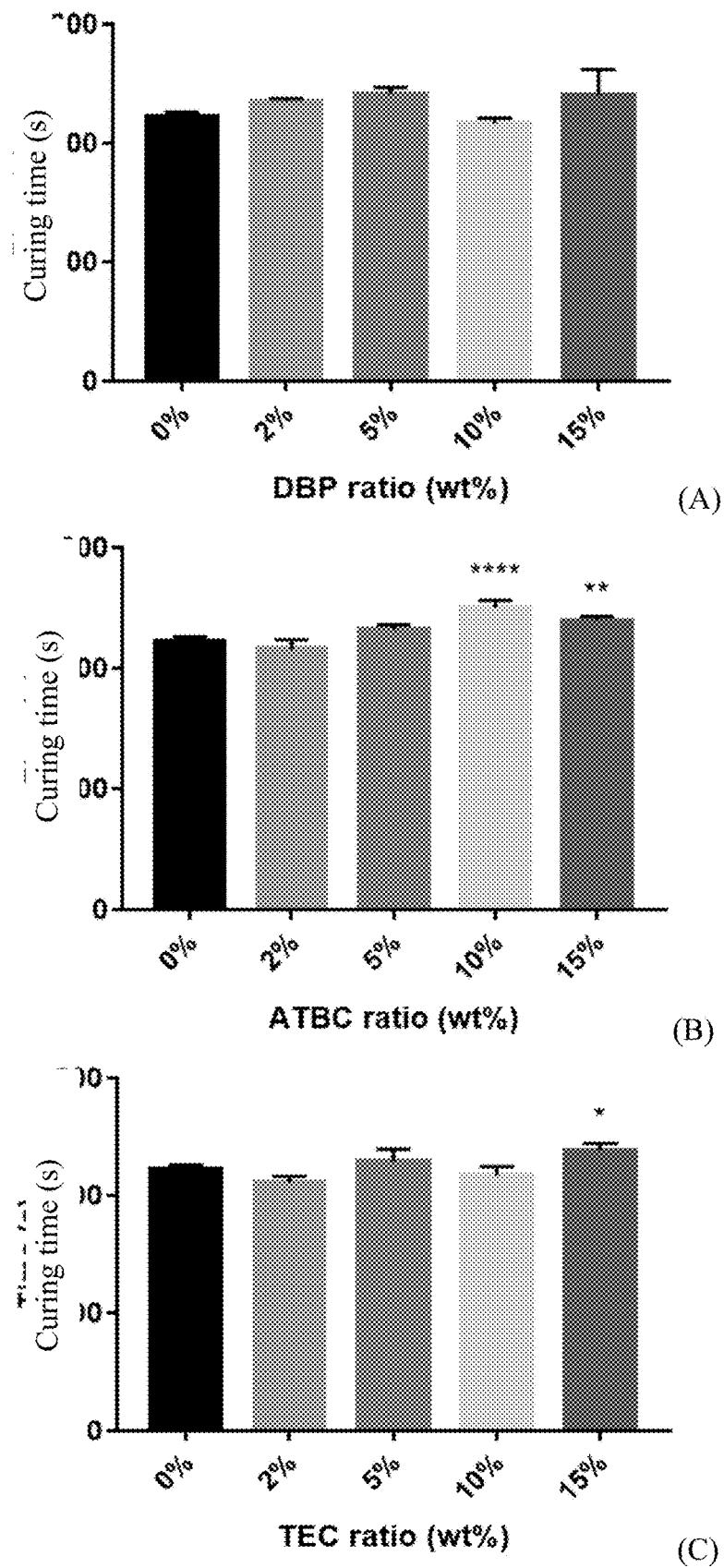
FIG. 2 shows the curing time tests of the temporary crown material compositions of the present invention, wherein (A) DBP, (B) ATBC, or (C) TEC is used as the plasticizers respectively.

FIG. 2 shows the curing time tests of the temporary crown material compositions, wherein (A) DBP, (B) ATBC, or (C) TEC is used as the plasticizers respectively. It can be seen from FIG. 2 that if the temporary crowns are prepared at room temperature, the curing time may vary due to the addition of plasticizers. In particular, the citrate ester plasticizer significantly increases the curing time, which is approximately 200 to 300 seconds.

Example 2 Cytotoxicity Test of the Temporary Crowns being Added with Plasticizers First, 2 grams (g) of the mixture of the powder reagent and the liquid reagent were taken to be cured and then immersed in 10 ml of MEM culture medium at a temperature of 37° C. for 24 hours. Afterwards, an extract of the mixture was taken, in which the extraction ratio was 0.2 g/ml.

Further, fibroblasts (L929) were seeded in the 96-well plates and incubated for 1 day. Each well plate had a cell density of $1\times10^4$ cells/100 μl MEM culture medium.

Afterwards, the cell culture media were removed, and then a material extract containing 10% fetal bovine serum (FBS) after filtration and a culture medium without the material extract as the control were added, respectively, and then incubated for 24-72 hours. Subsequently, the culture media were removed again, and then phosphate buffered saline (PBS) washes were performed, followed by PBS removal. The serum-free culture medium was formulated as a reaction reagent of MTT ((3-(4,5-dimethylthiazol-2-yl)-2,5-diphenyltetrazolium bromide)), and the ratio of the culture medium to the MTT solution was 1 mg/ml. Each well plate was added with 50 μl of MTT reagent and then placed in the incubator. After 2 hours, the MTT reagent was removed, and 100 μl of antifreezing agent (DMSO) was added. The 96-well plate was shaken for 30 minutes using a rotary shaker. After the reaction was completed, the absorbance at a wavelength of 570 nm was measured by an ELISA reader. The control is a commercially available temporary crown and bridge resin material, including ALIKE™ and Tempron™ and the cytotoxicity of dentures prepared with traditional plasticizers (DBP) was compared.

Figure 3:
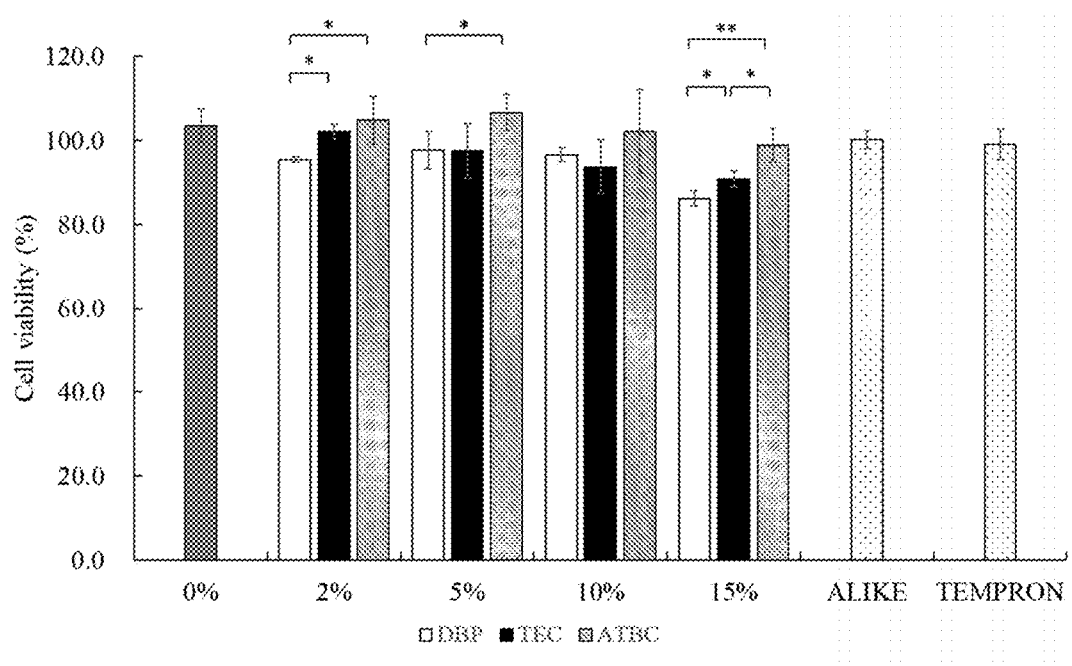
FIG. 3 shows the cytotoxicity test result of the temporary crown material compositions of the present invention, wherein the cell survival rate of the fibroblasts L929 co-cultured with the extract of the temporary crown material composition for (A) 24 hours and (B) 72 hours were recorded, respectively.
Figure 3:
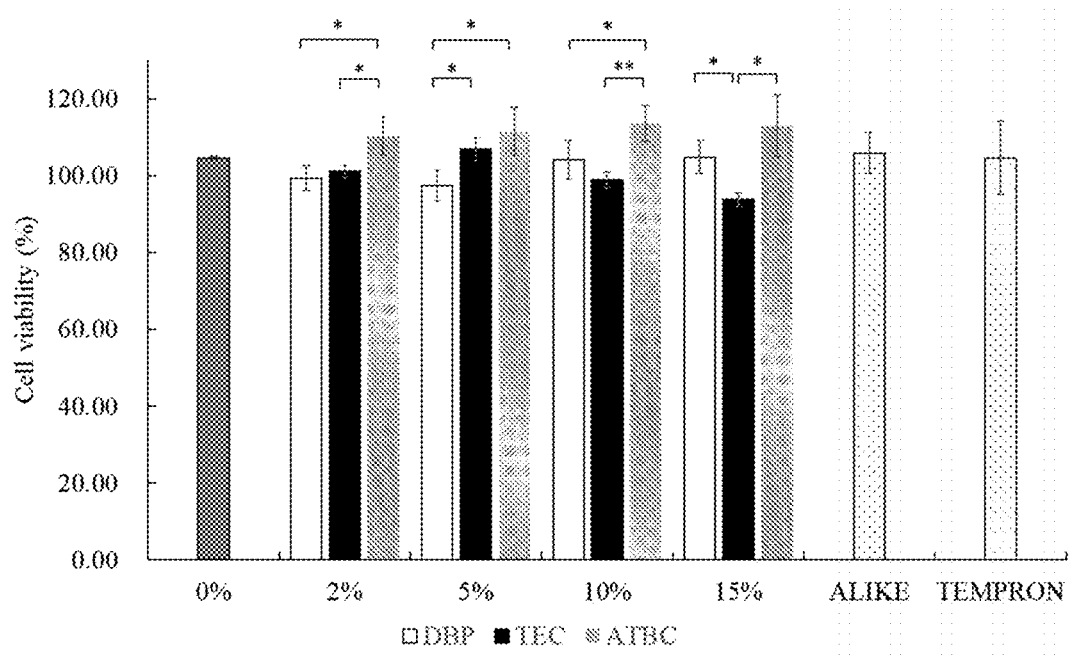

The results are showed in FIG. 3. FIG. 3 shows the cell survival rate of the fibroblasts L929 co-cultured with the extract of the temporary crown material composition for (A) 24 hours and (B) 72 hours, respectively. It can be observed that the cytotoxicity of adding plasticizers ATBC is less than that of adding plasticizers DBP and TEC, thereby having a higher survival rate. However, the cytotoxicity caused by TEC is not significantly improved, as compared with DBP (the statistical method: one-way analysis of variation (One-way ANOVA)).

It can be seen that the use of ATBC as a plasticizer causes less toxicity to cells.

Example 3 Three-Point Bending Test of the Temporary Crown Material with the Plasticizer Addition First, the temporary crown material was filled into a stainless steel mold (a length of 25 millimeters (mm), a width of 2 mm and a height of 2 mm). After the temporary crown was completely cured, the crown was immersed in ultrapure water and placed in an oven at 37° C. for 24 hours. After the crown was taken out, the sample to be tested was placed in a universal testing machine (Shimadzu autograph, AGS-500G), which had a sensor descending rate of 1 mm per minute for flexural strength test. The flexural strength was calculated by the following formula:

$$\sigma_B (\text{flexural strength}) = \frac{3Fl}{2bh^2}$$

wherein F was the force (N) under the maximum load; b was the average width (mm) of the test piece; h was the average thickness (mm) of the test piece; and l was the pitch (mm) between the two lower fulcrums.

Figure 4:
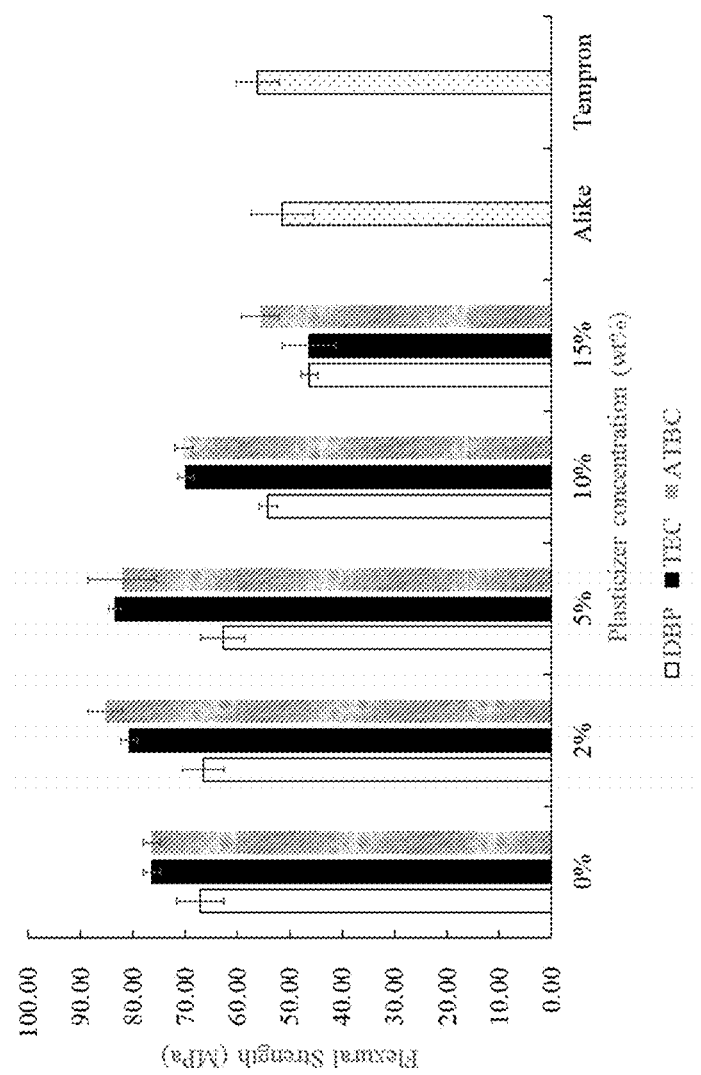
FIG. 4 shows the flexural strength test results of the temporary crowns of the present invention.

The results of the flexural strength test are showed in FIG. 4 and further in Table 1. In this example, the universal testing machine was used to perform the flexural strength test, and the effects on temporary crown samples' flexural strength of the added DBP, TEC, and ATBC were analyzed. According to FIG. 4, it is known that the addition of ATBC as the plasticizer can increase the flexural strength of the temporary crown, and is superior to the addition of DBP or TEC. The addition amount is preferably 0-5%, and no more than 10%.

In addition, the toughness of the temporary crown is the integral area under the stress-strain curve, in which stress is put on Y-axis and strain is put on X-axis. The unit of the toughness is $$\frac{J}{m^3},$$

i.e. MPa.

Figure 5:
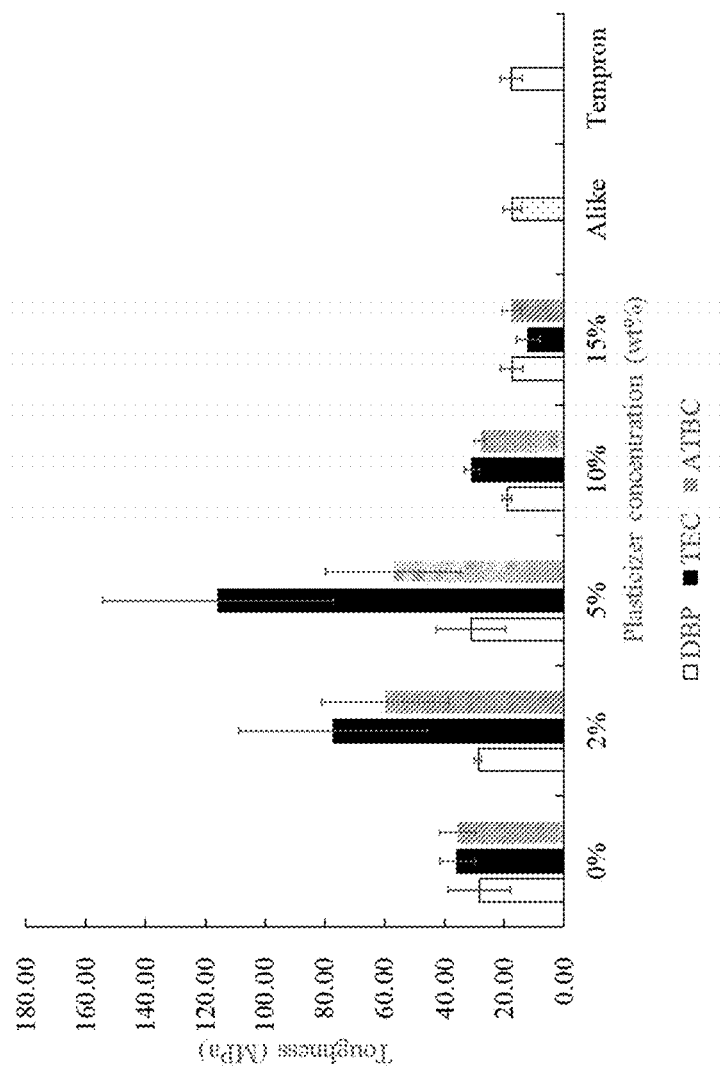
FIG. 5 shows the toughness test results of the temporary crowns of the present invention.

The toughness test results are showed in FIG. 5. In this example, the universal testing machine was used to perform the toughness test, and the effects on temporary crown samples' flexural strength of the added DBP, TEC, and ATBC were analyzed. According to FIG. 5, it is known that the addition of ATBC or TEC as the plasticizer can increase the toughness of the temporary crown, and is superior to the addition of DBP, in which TEC is superior to ATBC. The addition amount is preferably 0-5%, and no more than 10%.

In addition, Tables 1-3 disclose the quantified results of the three-point bending test of ATBC (Table 1), TEC (Table 2), and DBP (Table 3), respectively.

TABLE 1

|  | Maximum stress (MPa) | Flexural modulus (MPa) | Strain (%) | Elongation at break (%) | Toughness (MPa) |
| --- | --- | --- | --- | --- | --- |
| 0% | 76.44 ± 1.64 | 1782.30 ± 184.38 | 7.06 ± 0.67 | 7.06 ± 0.68 | 35.69 ± 6.01 |
| 2% | 85.24 ± 3.22 | 2463.34 ± 85.04 | 7.72 ± 0.65 | 7.94 ± 1.07 | 59.89 ± 21.21 |
| 5% | 81.98 ± 6.46 | 2362.61 ± 70.15 | 7.82 ± 0.96 | 8.24 ± 1.43 | 57.21 ± 22.40 |
| 10% | 70.29 ± 1.79 | 2138.92 ± 89.67 | 6.48 ± 0.28 | 6.50 ± 0.27 | 28.07 ± 1.80 |
| 15% | 55.59 ± 3.59 | 1897.78 ± 83.57 | 5.71 ± 0.26 | 5.70 ± 0.27 | 17.39 ± 3.19 |
| ALIKE | 51.43 ± 5.93 | 1466.27 ± 336.72 | 6.02 ± 0.39 | 6.02 ± 0.41 | 17.26 ± 2.96 |
| Tempron | 56.14 ± 4.09 | 1818.51 ± 207.46 | 5.32 ± 0.38 | 5.32 ± 0.38 | 17.43 ± 3.59 |

TABLE 2

|  | Maximum stress (MPa) | Flexural modulus (MPa) | Strain (%) | Elongation at break (%) | Toughness (MPa) |
| --- | --- | --- | --- | --- | --- |
| 0% | 76.44 ± 1.64 | 1782.30 ± 184.38 | 7.06 ± 0.67 | 7.06 ± 0.68 | 35.69 ± 6.01 |
| 2% | 80.70 ± 1.63 | 2173.29 ± 140.55 | 8.94 ± 0.93 | 10.43 ± 2.58 | 77.26 ± 31.45 |
| 5% | 83.40 ± 1.13 | 2308.16 ± 51.31 | 9.20 ± 0.20 | 13.14 ± 3.24 | 115.80 ± 38.55 |
| 10% | 69.93 ± 1.52 | 2029.32 ± 107.89 | 7.09 ± 0.21 | 7.10 ± 0.27 | 30.88 ± 2.44 |
| 15% | 46.31 ± 5.14 | 1790.09 ± 38.27 | 5.36 ± 0.44 | 5.34 ± 0.50 | 11.98 ± 3.94 |
| ALIKE | 51.43 ± 5.93 | 1466.27 ± 336.72 | 6.02 ± 0.39 | 6.02 ± 0.41 | 17.26 ± 2.96 |
| Tempron | 56.14 ± 4.09 | 1818.51 ± 207.46 | 5.32 ± 0.38 | 5.32 ± 0.38 | 17.43 ± 3.59 |

TABLE 3

|  | Maximum stress (MPa) | Flexural modulus (MPa) | Strain (%) | Elongation at break (%) | Toughness (MPa) |
| --- | --- | --- | --- | --- | --- |
| 0% | 67.16 ± 4.51 | 1243.68 ± 218.69 | 9.00 ± 1.83 | 8.92 ± 1.65 | 28.25 ± 10.57 |
| 2% | 66.56 ± 3.88 | 1215.08 ± 92.10 | 10.75 ± 0.50 | 10.86 ± 0.54 | 28.74 ± 1.29 |
| 5% | 62.75 ± 4.21 | 1199.73 ± 78.84 | 10.75 ± 1.50 | 11.43 ± 2.22 | 31.14 ± 11.73 |
| 10% | 54.11 ± 1.75 | 1083.70 ± 50.61 | 9.75 ± 0.50 | 9.56 ± 0.26 | 18.94 ± 1.56 |
| 15% | 46.25 ± 1.55 | 997.11 ± 45.38 | 9.50 ± 1.00 | 9.68 ± 1.07 | 17.35 ± 3.65 |
| Alike | 51.43 ± 5.93 | 1466.27 ± 336.72 | 6.02 ± 0.39 | 6.02 ± 0.41 | 17.26 ± 2.96 |
| Tempron | 56.14 ± 4.09 | 1818.51 ± 207.46 | 5.32 ± 0.38 | 5.32 ± 0.38 | 17.43 ± 3.59 |

Example 4 Hardness Test of Temporary Crowns

First, the temporary crown material was filled into a stainless steel mold (a diameter of 15 mm and a thickness of 1 mm). After the temporary crown was completely cured, the sample was immersed in ultrapure water and placed in an oven at 37° C. After 24 hours, the sample to be tested was taken out and placed in a micro hardness tester (HMV-2 series), and the load applied to the sample by the diamond indenter was 4.903 N for 10 seconds. Finally, the average length of the diagonal indentation on the surface of the sample was measured to calculate the surface hardness of the temporary crown. The calculation formula was:

$$HV(\text{Vickers Hardness}) = \frac{F}{s} = \frac{2F \times \sin\left(\frac{136°}{2}\right)}{g \times d^2},$$

wherein d is the length of the indentation, F is the load, and g is the gravity constant.

Figure 6:
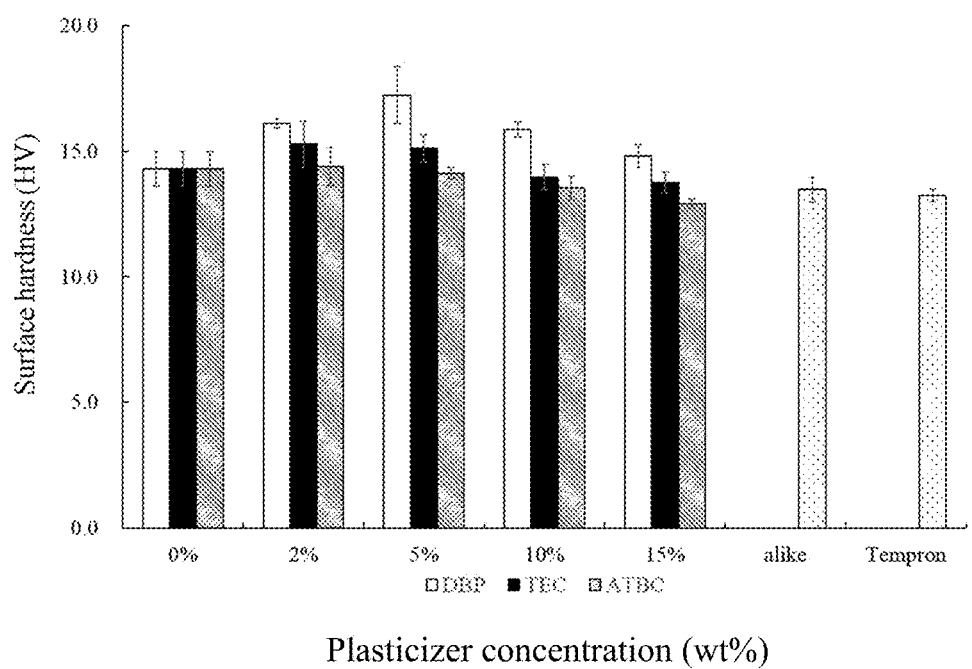
FIG. 6 shows the surface hardness test results of the temporary crowns of the present invention.

The hardness test results are showed in FIG. 6. This experiment used a micro hardness tester to measure the surface hardness of temporary crowns, and the effects on the temporary crowns' surface hardness of the added DBP, TEC, and ATBC as the plasticizers were compared. The DBP plasticizer at a low percentage contributes to the increase of surface hardness, and the overall p value is 0.0001. According to the literature, this is the so-called anti-plasticizing effect; while TEC and ATBC plasticizers also exhibited significant effects on the samples, in which the p values are 0.0148 and 0.0055, respectively.

As to the contents disclosed in the embodiments of the present specification, it is obvious for those of ordinary skill in the art that the foregoing embodiments are only examples but not limitations, and can be practiced by those of ordinary skill in the art through various variations or alterations without differing from the technical features of the present invention. In accordance with the described embodiments, many variations of the invention are possible without hindering the practice. The scope of the present invention is defined by the claims provided in the specification, and encompasses the aforementioned methods and structures and the equivalents thereof.

What is claimed is:

1. A composition of a temporary crown material, comprising: a powder reagent and a liquid reagent;

wherein the powder reagent comprises poly methyl methacrylate (PMMA) and an initiator; the liquid reagent comprises methyl methacrylate, a catalyst, and a plasticizer;

wherein the plasticizer is acetyl tributyl citrate.

2. The composition of claim 1, wherein the initiator is benzoyl peroxide (BPO).

3. The composition of claim 1, wherein the catalyst is N,N-dimethyl-p-toluidine (DMPT).

4. The composition of claim 1, wherein the ratio of the powder reagent to the liquid reagent is between 3:1 and 1:1 (W/V).

5. The composition of claim 1, wherein the powder reagent comprises 60-90% poly methyl methacrylate (PMMA), 1-5% benzoyl peroxide (BPO), 0-1% pigment, 0-1% opacifier, 0-20% plasticizer, and the rest being inorganic particles.

6. The composition of claim 1, wherein the liquid reagent comprises 1-5% catalyst, 0-20% crosslinking agent, 2-15% plasticizer, 0-0.1% inhibitor, 5-10% organic solvent, 5-10% UV absorber, and the rest being methyl methacrylate monomer (MMA).

7. The composition of claim 6, wherein the percentage of the plasticizer is between 2% and 10%.

8. A method for preparing a temporary crown, comprising:
   providing poly methyl methacrylate and an initiator, which are mixed to form a powder reagent;
   providing methyl methacrylate, a catalyst, and a plasticizer, which are mixed to form a liquid reagent;
   mixing the powder reagent with the liquid reagent to obtain a mixture; and
   placing the mixture at room temperature, which allows the mixture to cure, thereby obtaining a temporary crown;
   wherein the plasticizer is acetyl tributyl citrate.

9. The method of claim 8, wherein the powder reagent and the liquid reagent are mixed and placed at 20° C. to 25° C. to wait for the formation of the temporary crown.

\* \* \* \* \*